United States Patent
Brieaddy

[11] Patent Number: 5,859,240
[45] Date of Patent: Jan. 12, 1999

[54] HYPOLIPIDEMIC BENZOTHIAZEPINE COMPOUNDS

[75] Inventor: Lawrence Edward Brieaddy, Raleigh, N.C.

[73] Assignee: Glaxo Wellcome Inc., Research Triangle Park, N.C.

[21] Appl. No.: 919,980

[22] Filed: Aug. 28, 1997

Related U.S. Application Data

[62] Division of Ser. No. 290,805, Dec. 5, 1994, Pat. No. 5,663,165.

[30] Foreign Application Priority Data

Feb. 17, 1992 [GB] United Kingdom ............... 9203347

[51] Int. Cl.$^6$ ................................ C07D 281/10
[52] U.S. Cl. ........................................ 540/552
[58] Field of Search ............................. 540/552

[56] References Cited

U.S. PATENT DOCUMENTS

| | | | |
|---|---|---|---|
| 3,362,962 | 1/1968 | Reeder et al. | 260/294.8 |
| 3,503,985 | 3/1970 | Reeder et al. | 260/294.8 |
| 3,523,974 | 8/1970 | Reeder et al. | 260/591 |
| 3,530,139 | 9/1970 | Reeder et al. | 260/294.8 |
| 3,631,089 | 12/1971 | Reeder et al. | 260/455 |
| 5,276,025 | 1/1994 | Baldwin et al. | 514/211 |

OTHER PUBLICATIONS

Sternbach et al., "A New Type of 1,4–Benzothiazepine Derivatives," J. Org. Chem, 30(8), 2812–2818 (1965).
Nair et al., "Synthesis & Reactions of Benz[1,4]thiazepine Derivatives," 7(9), 862–865 (1969).
Grundy, "Cholesterol and Coronary Heart Disease," J. Amer. Med. Assn., 256(20), 2849–2859 (1986).
Sugano et al., "Suppression of Atherosclerosis in Cholesterol–Fed Rabbits by Diltiazem Injection," Arteriosclerosis, 6(2), 237–241(1986).
"Pharmaceutical Compounds," Research Disclosure 35450, 691–693 (Oct. 1993).
Szabo et al., "Synthesis and Spectroscopic Investigation of 1,4–Benzothiazepine Derivatives," Chemical Abstracts, 108:221680x (1988).
Szabo et al., "Saturated Heterocycles. Part 116. Synthesis and Spectroscopic Investigations of 1,4–Benxothiazepine Derivatives," Heterocycles, 108:5984g (1988).

Primary Examiner—Mukund J. Shah
Assistant Examiner—Bruck Kifle
Attorney, Agent, or Firm—Lorie Ann Morgan; Robert T. Hrubiec

[57] ABSTRACT

The present invention is concerned with processes for preparing hypolipidaemic benzothiazepine compounds of formula (I)

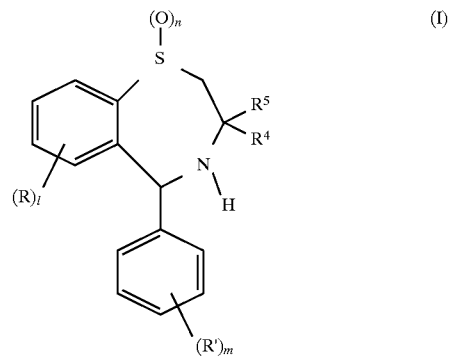

wherein l is an integer of from 0 to 4; m is an integer of from 0 to 5; n is an integer of from 0 to 2; R and R' are atoms or groups independently selected from halogen, nitro, phenylalkoxy, $C_{1-4}$ alkoxy, $C_{1-6}$ alkyl and $—O(CH_2)_pSO_3R"$ wherein p is an integer of from 1 to 4 and R" is hydrogen or $C_{1-6}$ alkyl, wherein said phenylalkoxy, alkoxy and alkyl groups are optionally substituted by one or more halogen atoms; $R^4$ is $C_{1-6}$ straight alkyl group; and $R^5$ is a $C_{2-6}$ straight alkyl group; and their salts, solvates and physiologically functional derivatives; and intermediates useful in said processes.

2 Claims, No Drawings

HYPOLIPIDEMIC BENZOTHIAZEPINE COMPOUNDS

This application is a division of application Ser. No. 08/290,805, filed Dec. 5, 1994, now U.S. Pat. No. 5,663,165.

The present invention is concerned with new hypolipidaemic compounds, with processes and novel intermediates for their preparation, with pharmaceutical compositions containing them and with their use in medicine, particularly in the prophylaxis and treatment of hyperlipidaemic conditions, such as atherosclerosis.

Hypolipidaemic conditions are often associated with elevated plasma concentrations of low density lipoprotein (LDL) cholesterol and very low density lipoprotein (VLDL) cholesterol. Such concentrations may be reduced by decreasing the absorption of bile acids from the intestine. One method by which this may be achieved is to inhibit the bile acid active uptake system in the terminal ileum. Such inhibition stimulates the conversion of cholesterol to bile acid by the liver and the resulting increase in demand for cholesterol produces a corresponding increase in the rate of clearance of LDL and VLDL cholesterol from the blood plasma or serum.

There has now been identified a novel class of heterocyclic compounds which reduce the plasma or serum concentrations of LDL and VLDL cholesterol and in consequence are particularly useful as hypolipidaemic agents. By decreasing the concentrations of cholesterol and cholesterol ester in the plasma, the compounds of the present invention retard the build-up of atherosclerotic lesions and reduce the incidence of coronary heat disease-related events. The latter are defined as cardiac events associated with increased concentrations of cholesterol and cholesterol ester in the plasma or serum.

For the purposes of this specification, a hyperlipidaemic conditions is defined as any condition wherein the total cholesterol concentrations (LDL+VLDL) in the plasma or serum is greater than 240 mg/dL (6.21 mmol/L) (J. Amer. Med. Assn. 256, 20, 2849–2858 (1986)).

U.S. Pat. No. 3,362,962 describes a genus of benzothiazepines outside the scope of the present invention which have muscle-relaxant and anticonvulsant activity; there is no disclosure in the patent specification that the compounds described therein may be useful as hypolipidaemic agents.

According to the present invention, there is provided a compound of formula (I)

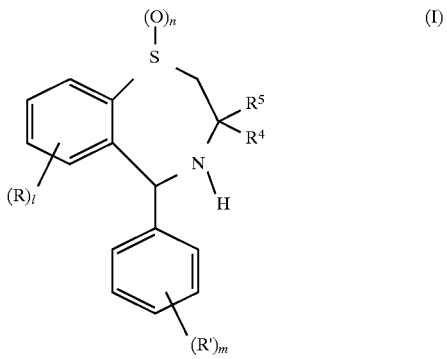

wherein
l is an integer of from 0 to 4;
m is an integer of from 0 to 5;
n is an integer of from 0 to 2;
R and R' are atoms or groups independently selected from halogen, nitro, phenylalkoxy, $C_{1-4}$ alkoxy, $C_{1-6}$ alkyl and —O(CH$_2$)$_p$SO$_3$R" wherein p is an integer of from 1 to 4 and R" is hydrogen or $C_{1-6}$ alkyl, wherein said phenylalkoxy, alkoxy and alkyl groups are optionally substituted by one or more halogen atoms;
$R^4$ is a $C_{1-6}$ straight alkyl group; and
$R^5$ is a $C_{2-6}$ straight alkyl group;
and salts, solvates and physiologically functional derivatives thereof.

Pharmaceutically acceptable salts are particularly suitable for medical applications because of their greater aqueous solubility relative to the parent, i.e. basic, compounds. Such salts must clearly have a pharmaceutically acceptable anion or cation. Suitable pharmaceutically acceptable acid addition salts of the compounds of the present invention include those derived from inorganic acids, such as hydrochloric, hydrobromic, phosphoric, metaphosphoric, nitric, sulphonic and sulphuric acids, and organic acids, such as acetic, benzenesulphonic, benzoic, citric, ethanesulphonic, fumaric, gluconic, glycollic, isothionic, lactic, lactobionic, maleic, malic, methanesulphonic, succinic, p-toluenesulphinic, tartaric and trifluoroacetic acids. The chloride salt is particularly preferred for medical purposes. Suitable pharmaceutically acceptable base salts include ammonium salts, alkali metal salts, such as sodium and potassium salts, and alkaline earth salts, such as magnesium and calcium salts.

Salts having a non-pharmaceutically acceptable anion are within the scope of the invention as useful intermediates for the preparation or purification of pharmaceutically acceptable salts and/or for use in non-therapeutic, for example, in vitro, applications.

The term "physiologically functional derivative" as used herein refers to any physiologically acceptable derivative of a compound of the present invention, for example, an ester, which upon administration to a mammal, such as a human, is capable of providing (directly or indirectly) such a compound or an active metabolite thereof.

A further aspect of the invention is prodrugs of the compounds of the invention. Such prodrugs can be metabolised in vivo to give a compound according to the invention. These prodrugs may or may not be active in their own right.

The compounds of the present invention can also exist in different polymorphic forms, for example, amorphous and crystalline polymorphic forms. All polymorphic forms of the compounds of the present invention are within the scope of the invention and are a further aspect thereof.

The term "alkyl" as used herein refers, unless otherwise stated, to a monovalent straight or branched chain radical. Likewise, the term "alkoxy" refers to a monovalent straight or branched chain radical attached to the parent molecular moiety through an oxygen atom. The term "phenylalkoxy" refers to a monovalent phenyl group attached to a divalent $C_{1-6}$ alkylene group which is itself attached to the parent molecular moiety through an oxygen atom.

The compounds of formula (I) may exist in forms wherein one or both of the carbon centres —C(R$^4$)(R$^5$)- and —CHPh(R')$_m$- (wherein Ph is the phenyl group) is/are chiral. The present invention includes within its scope each possible optical isomer substantially free, i.e. associated with less than 5%, of any other optical isomer(s), and mixtures of one or more optical isomers in any proportions, including racemic mixtures.

For the purposes of this specification, the absolute chiralities of the aforementioned carbon centres are given in the order —C(R$^4$)(R$^5$)-, then —CHPh(R')$_m$-. For example, the prefix "(RS)-" denotes an (R)-configuration at —C(R$^4$)(R$^5$)- and an (S)-configuration at —CHPh(R')$_m$- and the prefix "(RS,SR)-" denotes a mixture of two isomers wherein one is (R)- at —C(R$^4$)(R$^5$)- and (S)- at —CHPh(R')$_m$- and the other is (S)- at —C(R$^4$)(R$^5$)- and (R)- at —CHPh(R')$_m$-. Other permutations will be clear to the skilled person.

In those cases where the absolute stereochemistry at —C($R^4$)($R^5$)— and —CHPh(R')$_m$— has not been determined, the compounds of the invention are defined in terms of the relative positions of the $R^4$/$R^5$ and H/Ph(R')$_m$ substituents. Thus those compounds wherein the bulkier of the $R^4$ and $R^5$ substituents, i.e. the substituent of higher mass, and the Ph(R')$_m$ substituent are both located on the same side of the thiazepine ring are referred to herein as "cis", and those compounds in which they are located on opposite sides of the ring are referred to as "trans". It will be evident to a skilled person that both "cis" and "trans" compounds of the invention can each exist in two enantiomeric forms which are individually designated "(+)-" or "(−)-" according to the direction of rotation of a plane of polarised light when passed through a sample of the compound. Cis or trans compounds of the invention in which the individual enantiomers have not been resolved are referred to herein using the prefix "(+−)-".

Preferred compounds of formula (I) having particularly desirable hypolipidaemic properties include those wherein n is 2;

$R^4$ is methyl, ethyl, n-propyl, or n-butyl; and/or $R^5$ is ethyl, n-propyl, or n-butyl.

Of these, the (RR)-, (SS)-, and (RR,SS)-trans compounds are particularly preferred.

A compound of formula (I) having exceptional hypolipidaemic properties is trans-3-butyl-3-ethyl-2,3,4,5-tetrahydro-5-phenyl-1,4-benzothiazepine 1,1-dioxide in both its (RR)- and (RR,SS)-forms, viz (−)-(RR)-3-butyl-3-ethyl-2,3,4,5-tetrahydro-5-phenyl-1,4-benzothiazepine 1,1-dioxide and (+−)-trans-3-butyl-3-ethyl-2,3,4,5-tetrahydro-5-phenyl-1,4-benzothiazepine 1,1-dioxide respectively. The former is especially preferred and is depicted thus:

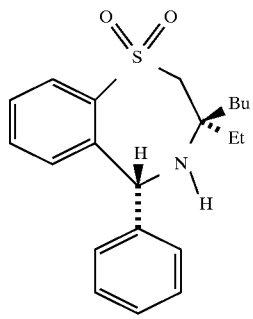

According to further aspects of the invention, there are also provided:

(a) compounds of formula (I) and pharmaceutically acceptable salts, solvates and physiologically functional derivatives thereof for use as therapeutic agents, particularly in the prophylaxis and treatment of clinical conditions for which a bile acid uptake inhibitor is indicated, for example, a hyperlipidaemic condition, such as atherosclerosis;

(b) pharmaceutical compositions comprising a compound of formula (I) or one of its pharmaceutically acceptable salts, solvates, or physiologically functional derivatives, at least one pharmaceutically acceptable carrier and, optionally, one or more other physiologically active agents;

(c) the use of a compound of formula (I) or of a pharmaceutically acceptable salt, solvate, or physiologically functional derivative thereof in the manufacture of a medicament for the prophylaxis or treatment of a clinical condition for which a bile acid uptake inhibitor is indicated, for example, a hyperlipidaemic condition, such as atherosclerosis;

(d) a method of inhibiting the absorption of bile acids from the intestine of a mammal, such as a human, which comprises administering an effective bile acid absorption inhibiting amount of a compound of formula (I) or of a pharmaceutically acceptable salt, solvate, or physiologically functional derivative thereof to the mammal;

(e) a method of reducing the blood plasma or serum concentrations of LDL and VLDL cholesterol in a mammal, such as a human, which comprises administering an effective cholesterol reducing amount of a compound of formula (I) or of a pharmaceutically acceptable salt, solvate, or physiologically functional derivative thereof to the mammal;

(f) a method of reducing the concentrations of cholesterol and cholesterol ester in the blood plasma or serum of a mammal, such as a human, which comprises administering an effective cholesterol and cholesterol ester reducing amount of a compound of formula (I) or of a pharmaceutically acceptable salt, solvate, or physiologically functional derivative thereof to the mammal;

(g) a method of increasing the faecal excretion of bile acids in a mammal, such as a human, which comprises administering an effective bile acid faecal excretion increasing amount of a compound of formula (I) or of a pharmaceutically acceptable salt, solvate, or physiologically functional derivative thereof to the mammal;

(h) a method for the prophylaxis or treatment of a clinical condition in a mammal, such as a human, for which a bile acid uptake inhibitor is indicated, for example, a hyperlipidaemic condition, such as atherosclerosis, which comprises administering a therapeutically effective amount of a compound of the formula (I), or of a pharmaceutically acceptable salt, solvate, or physiologically functional derivative thereof to the mammal;

(i) a method of reducing the incidence of coronary heart disease-related events in a mammal, such as a human, which comprises administering an effective coronary heart disease-related events reducing amount of a compound of formula (I) or of a pharmaceutically acceptable salt, solvate, or physiologically functional derivative thereof;

(j) a method of reducing the concentration of cholesterol in the blood plasma or serum of a mammal, such as a human, which comprises administering an effective cholesterol reducing amount of a compound of formula (I);

(k) processes for the preparation of compounds of formula (I) (including salts, solvates and physiologically functional derivatives thereof as defined herein); and (l) compounds of formula (II) for use as intermediates in the preparation of compounds of formula (I).

Hereinafter all references to "compound(s) of formula (I)" refer to compound(s) of formula (I) as described above together with their salts, solvates and physiologically functional derivatives as defined herein.

The amount of a compound of formula (I) which is required to achieve the desired biological effect will, of course, depend on a number of factors, for example, the specific compound chosen, the use for which it is intended, the mode of administration and the clinical condition of the recipient. In general, a daily dose is in the range of from 0.3 mg to 100 mg (typically from 3 mg to 50 mg) per day per kilogram bodyweight, for example, 3–10 mg/kg/day. An intravenous dose can, for example, be in the range of from 0.3 mg to 1.0 mg/kg, which can conveniently be administered as an infusion of from 10 ng to 100 ng per kilogram per minute. Infusion fluids suitable for this purpose can contain, for example, from 0.1 ng to 10 mg, typically from 1 ng to 10 mg, per millilitre. Unit doses can contain, for example, from 1 mg to 10 g of the active compound. Thus ampoules for injection can contain, for example, from 1 mg to 100 mg and orally administrable unit dose formulations, such as tablets or capsules, may contain, for example, from 1.0 to 1000 mg, typically from 10 to 600 mg. In the case of pharmaceutically acceptable salts, the weights indicated above refer to the weight of the benzothiazepine ion derived from the salt.

For the prophylaxis or treatment of the conditions referred to above, the compounds of formula (I) can be used as the compound per se, but are preferably presented with an acceptable carrier in the form of a pharmaceutical composition. The carrier must, of course, be acceptable in the sense of being compatible with the other ingredients of the composition and must not be deleterious to the recipient. The carrier can be a solid or a liquid, or both, and is preferably formulated with the compound as a unit-dose composition, for example, a tablet, which can contain from 0.05% to 95% by weight of the active compound. Other pharmaceutically active substances can also be present including other compounds of formula (I). The pharmaceutical compositions of the invention can be prepared by any of the well known techniques of pharmacy consisting essentially of admixing the components.

Pharmaceutical compositions according to the present invention include those suitable for oral, rectal, tropical, buccal (e.g. sub-lingual) and parenteral (e.g. subcutaneous, intramuscular, intradermal, or intravenous) administration, although the most suitable route in any given case will depend on the nature and severity of the condition being treated and on the nature of the particular compound of formula (I) which is being used. Enteric-coated and enteric-coated controlled release formulations are also within the scope of the invention. Suitable enteric coatings include cellulose acetate phthalate, polyvinylacetate phthalate, hydroxypropylmethylcellulose phthalate and anionic polymers of methacrylic acid and methacrylic acid methyl ester.

Pharmaceutical compositions suitable for oral administration can be presented in discrete units, such as capsules, cachets, lozenges, or tablets, each containing a predetermined amount of a compound of formula (I); as a powder or granules; as a solution or a suspension in an aqueous or non-aqueous liquid; or as an oil-in-water or water-in-oil emulsion. As indicated, such compositions can be prepared by any suitable method of pharmacy which includes the step of bringing into association the active compound and the carrier (which can constitute one or more accessory ingredients). In general, the compositions are prepared by uniformly and intimately admixing the active compound with a liquid or finely divided solid carrier, or both, and then, if necessary, shaping the product. For example, a tablet can be prepared by compressing or moulding a powder or granules of the compound, optionally with one or more accessory ingredients. Compressed tablets can be prepared by compressing, in a suitable machine, the compound in a free-flowing form, such as a powder or granules optionally mixed with a binder, lubricant, inert diluent and/or surface active/dispersing agent(s). Moulded tablets can be made by moulding, in a suitable machine, the powdered compound moistened with an inert liquid diluent.

Pharmaceutical compositions suitable for buccal (sub-lingual) administration include lozenges comprising a compound of formula (I) in a flavoured base, usually sucrose and acacia or tragacanth, and pastilles comprising the compound in an inert base such as gelatin and glycerin or sucrose and acacia.

Pharmaceutical compositions suitable for parenteral administration conveniently comprise sterile aqueous preparations of a compound of formula (I), preferably isotonic with the blood of the intended recipient. These preparations are preferably administered intravenously, although administration can also be effected by means of subcutaneous, intramuscular, or intradermal injection. Such preparations can conveniently be prepared by admixing the compound with water and rendering the resulting solution sterile and isotonic with the blood. Injectable compositions according to the invention will generally contain from 0.1 to 5% w/w of the active compound.

Pharmaceutical compositions suitable for rectal administration are preferably presented as unit-dose suppositories. These can be prepared by admixing a compound of formula (I) with one or more conventional solid carriers, for example, cocoa butter, and then shaping the resulting mixture.

Pharmaceutical compositions suitable for topical applications to the skin preferably take the form of an ointment, cream, lotion, paste, gel, spray, aerosol, or oil. Carriers which can be used include vaseline, lanoline, polyethylene glycols, alcohols, and combinations of two or more thereof. The active compound is generally present at a concentration of from 0.1 to 15% w/w of the composition, for example, from 0.5 to 2%.

Transdermal administration is also possible. Pharmaceutical compositions suitable for transdermal administration can be presented as discrete patches adapted to remain in intimate contact with the epidermis of the recipient for a prolonged period of time. Such patches suitably contain the active compound in an optionally buffered, aqueous solution, dissolved and/or dispersed in an adhesive, or dispersed in a polymer. A suitable concentration of the active compound is about 1% to 35%, preferably about 3% to 15%. As one particular possibility, the active compound can be delivered from the patch by electrotransport or iontophoresis, for example, as described in *Pharmaceutical Research*, 3(6), 318 (1986).

The compounds of the invention can be prepared by conventional methods known to a skilled person or in an analogous manner to processes described in the art.

For example, compounds of formula (I) wherein n=0 can be prepared by reducing the imine bond of a compound of formula (II)

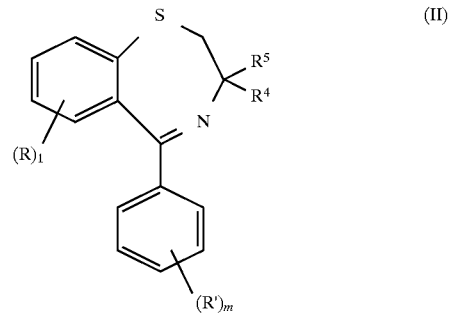

wherein l, m, R, R', $R^4$ and $R^5$ are as hereinbefore defined, using, for example, a boron compound, such as borane, in a suitable solvent, such as THF, or catalytic hydrogenation using, for example, a palladium catalyst, such as 10% Pd/C.

Compounds of formula (II) as herein defined are considered to be novel and constitute a further aspect of the present invention.

Compounds of formula (II) can be prepared by cyclising compounds of formula (III)

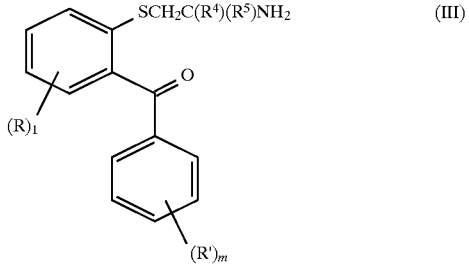

wherein l, m, R, R', $R^4$ and $R^5$ are as hereinbefore defined, by, for example, azeotropic distillation or refluxing in the presence of a suitable drying agent, such as molecular sieves, in a suitable solvent, for example, 2,6-lutidine, in the presence of an acid, such as HCl.

Compounds of formula (III) can be prepared by reacting a compound of formula (IV)

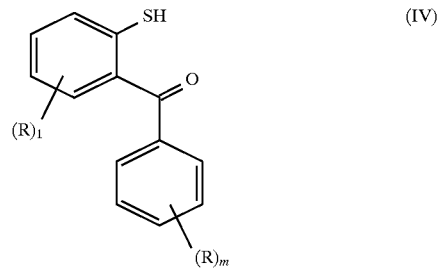

wherein l, m, R and R' are as hereinbefore defined, with a compound of formula (V)

wherein $R^4$ and $R^5$ are as hereinbefore defined, typically in a polar solvent, for example, methanol.

Compounds of formula (III) can also be prepared by reacting a compound of formula (XVIII)

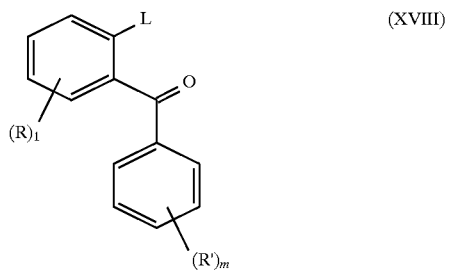

wherein l, m, R and R' are as hereinbefore defined and L is a suitable leaving group, for example, halogen, with a compound of formula $HSCH_2C(R^4)(R^5)NH_2$ wherein $R^4$ and $R^5$ are as hereinbefore defined.

Compounds of formula (XVIII) can be prepared by reacting a compound of formula (XIX)

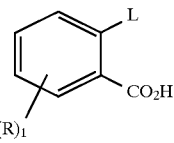

wherein l, L and R are as hereinbefore defined, with a compound of formula $Ph(R')_mH$ wherein Ph is a phenyl group and m and R' are as hereinbefore defined, typically by a Friedel-Crafts reaction using, for example, aluminium chloride.

Compounds of formula (IV) can be prepared by reacting a compound of formula (VI)

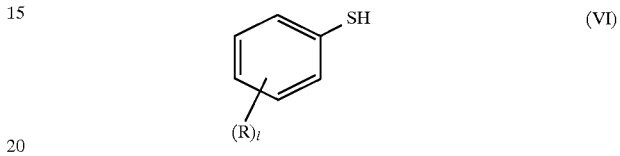

wherein l and R are as hereinbefore defined, with a compound of formula $(R')_mPhCN$ wherein Ph is a phenyl group and m and R' are as hereinbefore defined. The reaction is typically carried out by lithiation of compound (VI) using, for example, n-butyl lithium in the presence of N,N,N',N'-tetramethylethylenediamine (TMEDA) followed by reaction with the appropriate benzonitrile in a non-polar solvent, for example, cyclohexane.

Compounds of formula (IV) can also be prepared by reacting a compound of formula (XVIII) as hereinbefore defined with sodium sulphide.

Compounds of formulae (V), (XIX), (VI) and $(R')_mPhCN$ as hereinbefore defined can be obtained commercially or prepared by method known to those skilled in the art or obtainable from the chemical literature. Thus compounds of formula (V) can be prepared from the corresponding 2-substituted 2-aminoethanols.

Compounds of formula (I) wherein n=0 can also be prepared by cyclising a compound of formula (VIII)

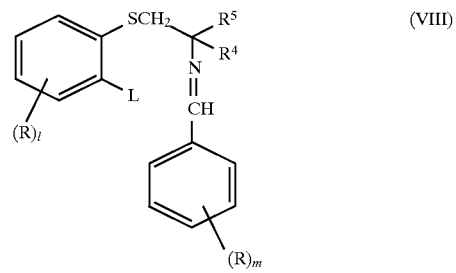

wherein l, m, R, R', $R^4$ and $R^5$ are as hereinbefore defined and L' is halogen, for example, bromine, by treatment with strong base, for example, n-butyl lithium, in a suitable solvent, such as THF, at a low temperature, for example, −78° C.

Compounds of formula (VIII) can be prepared by reaction of a compound of formula (IX)

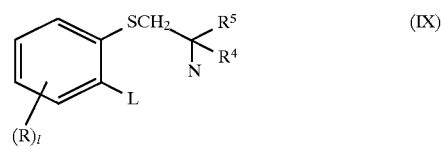

wherein l, L', R, $R^4$ and $R^5$ are as hereinbefore defined, with a compound of formula $(R')_mPhCHO$ wherein Ph is a phenyl group and m and R' are as hereinbefore defined. The reaction is typically carried out in a non-polar solvent, for example, toluene, in the presence of an acid, such as p-toluenesulphonic acid.

Compounds of formula (IX) can be prepared by reacting a compound of formula (XI)

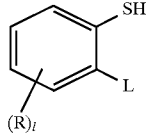

wherein l, L' and R are as hereinbefore defined, with a compound of formula (V) wherein $R^4$ and $R^5$ are as hereinbefore defined, typically in a polar solvent, such as methanol.

Compounds of formula (IX) can also be prepared by reacting a compound of formula (XI) as hereinbefore defined with a compound of formula (XVII)

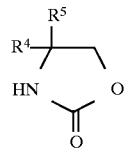

wherein $R^4$ and $R^5$ are as hereinbefore defined, in the presence of a Lewis acid, for example, lithium chloride, at an elevated temperature, such as 170°–210° C.

Compounds of formulae $(R')_m$PhCHO as hereinbefore defined, (XI) and (XVII) can be obtained commercially or prepared by methods known to those skilled in the art or obtainable from the chemical literature. Thus compounds of formula (XI) may be prepared from the corresponding disulphides and compounds of formula (XVII) from the corresponding 2-substituted 2-aminoethanols.

Compounds of formula (I) wherein n=0 can also be obtained by phenylating a compound of formula (XIII)

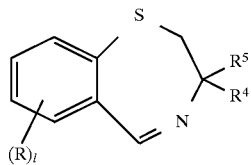

wherein l, R, $R^4$ and $R^5$ are as hereinbefore defined, using, for example, an organometallic compound, such as $(R')_m$PhLi, $(R')_m$PhCu, $(R')_m$PhZn, or $(R')_m$PhMgBr wherein Ph is a phenyl group and m and R' are as hereinbefore defined.

Compounds of formula (XIII) can be prepared by dehydrogenating the corresponding compound of formula (XIV)

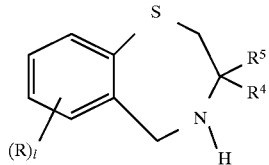

wherein l, R, $R^4$ and $R^5$ are as hereinbefore defined, using, for example, an oxidising agent, such as 2,3-dichloro-5,6-dicyano-1,4-benzoquinone (DDQ), in a suitable solvent, for example, toluene.

Compounds of formula (XIV) can be prepared by reducing the amide carbonyl group of the corresponding compound of formula (XV)

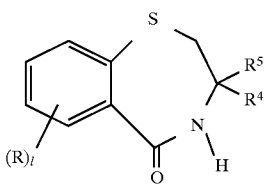

wherein l, R, $R^4$ and $R^5$ are as hereinbefore defined, using, for example, lithium aluminium hydride.

compounds of formula (XV) can be prepared by reacting a compound of formula (XVI)

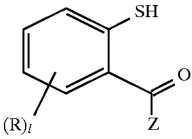

wherein l and R are as hereinbefore defined and Z is $C_{1-4}$ alkoxy, for example, methoxy, with a compound of formula (V) wherein $R^4$ and $R^5$ are as hereinbefore defined.

The compound of formula (XVI) wherein l=0 can be prepared from commercially available 2,2'-dithiosalicyclic acid by methods known to those skilled in the art. Compounds of formula (XVI) wherein l≠0 can be obtained commercially or prepared by methods known to those skilled in the art or obtainable from the chemical literature.

Compounds of formula (I) wherein n=1 or 2 can be prepared by oxidation of the corresponding compound of formula (I) wherein n=0 or by oxidation of the corresponding compound of formula (III) wherein n=0 prior to cyclisation and reduction to the compound of formula (I) using suitable oxidation conditions, for example, in the case wherein n is to be 2, 30% aqu. $H_2O_2$ in the presence of trifluoroacetic acid.

Individual optical isomers of compounds of formula (I) substantially free, of other optical isomers can be obtained either by chiral synthesis, for example, by the use of the appropriate chiral starting material(s), such as the aziridine (V), or by resolution of the products obtained from achiral syntheses, for example, by chiral hplc.

Optional conversion of a compound of formula (I) to a corresponding acid addition salt may be effected by reaction with a solution of the appropriate acid, for example, one of those recited earlier. Optional conversion to a corresponding base salt may be effected by reaction with a solution of the appropriate base, for example, sodium hydroxide. Optional conversion to a physiologically functional derivative, such as an ester, can be carried out by methods known to those skilled in the art or obtainable from the chemical literature.

For a better understanding of the invention, the following Examples are given by way of illustration and are not to be construed in any way as limiting the scope of the invention.

SYNTHETIC EXAMPLE 1

Preparation of (−)-(RR)-3-butyl-3-ethyl-2,3,4,5-terahydro-5-phenyl-1,4-benzothiazepine 1,1-dioxide (a) Ethyl 2-aminobutyrate hydrochloride A slurry of 2-aminobutyric acid (100 g, Aldrich) in absolute ethanol (300 ml) was stirred under nitrogen at 0° C. and thionyl chloride (120.79 g) was added dropwise. The reaction was stirred overnight at 0° C. and then gradually warmed to room temperature. The resulting white slurry was heated under reflux for 3 hours, left to cool for 10 minutes, then poured into chilled diethyl ether (600 ml) with hand stirring. The suspension was filtered and the solid product dried to give the desired product (150 g) as a white solid. $^1$H NMR consistent with proposed structure.

(b) Ethyl 2-benzylideneaminobutyrate

A solution of the product from step (a) (149.57 g), magnesium sulphate (74.32 g), and triethylamine (246 ml) in dichloromethane (1500 ml) was stirred at room temperature under nitrogen and benzaldehyde (94.91 g, Aldrich) was added dropwise. The mixture was stirred at room temperature for 3 hours then filtered. The filtrate was concentrated, triturated in diethyl ether, filtered and concentrated to yield the desired product as a yellow oil (174 g). $^1$H NMR consistent with the proposed structure.

(c) Ethyl 2-benzylideneamino-2-ethylhexanoate

Sodium hydride (32.49 g, 60% dispersion in oil) and N,N-Dimethylformamide (DMF) (700 ml) were stirred under nitrogen at room temperature and a solution of the product from (b) (178.13 g) in DMF was added dropwise. After 2 hours stirring at room temperature, a solution of butyl iodide (149.48 g) in DMF was added dropwise and the reaction left stirring for a further 2 hours. The reaction was poured into an ice cold mixture of water (560 ml), diethyl ether (300 ml) and ammonium chloride (120 g). The resulting organic layer was dried over potassium carbonate then concentrated to give the desired product as a brown oil (220 g).

(d) Ethyl 2-amino-2-ethylhexanoate

The product from (c) (233.02 g) was partitioned between petroleum ether and 10% w/w hydrochloric acid (421 ml) and stirred at room temperature for 2 hours. The aqueous layer was extracted twice with petroleum ether and then chilled with ethyl acetate in an ice-salt bath. Sodium hydroxide pellets were added to the mixture until the aqueous layer was at pH 10. The latter was extracted twice with ethyl acetate and the combined ethyl acetate layers were dried over potassium carbonate, then concentrated and vacuum distilled to give the desired product as a colourless oil. $^1$H NMR consistent with the proposed structure.

(e) 2-Amino-2-ethylhexan-1-ol

Lithium aluminium hydride (22.22 g) was added to anhydrous diethyl ether (450 ml) under nitrogen. The product from (d) (129.0 g) was diluted with diethyl ether (40 ml) and added dropwise. The reaction was refluxed for 1 hour then cooled to room temperature. 1M sodium hydroxide (23 ml) was added dropwise followed by deionised water. The resulting suspension was filtered and the filtrate concentrated to give the desired product as a colourless oil (87.9 g). $^1$H NMR consistent with the proposed structure.

(f) 2-Butyl-2-ethylaziridine

Acetonitrile (150 ml) and the product from (e) (20.0 g) were mixed under nitrogen, cooled to 2°–3° C. and chlorosulphonic acid (16.04 g, Aldrich) was added dropwise keeping the temperature below 10° C. The coolant was removed and the slurry left to stir for 80 minutes at room temperature. The reaction was concentrated in vacuo and co-distilled with water (50 ml). 50% Aqueous sodium hydroxide (55.2 g) and water (50 ml) were added and the mixture was distilled at atmospheric pressure. The organic layer was collected from the distillate and dried with solid potassium hydroxide to give the desired product (12.8 g). $^1$H NMR consistent with proposed structure.

(g) 2-Thiobenzophenone

A solution of N,N,N',N'-tetramethylethylenediamine (TMEDA) (104.6 g) in cyclohexane (500 ml) was cooled and 2.5M n-butyl lithium (360 ml) was added. A solution of thiophenol (50.0 g) in cyclohexane (100 ml) was added slowly to the butyl lithium solution and the reaction was stirred at room temperature overnight. Benzonitrile (46.4 g, Aldrich) in cyclohexane (100 ml) was added to give a slurry which was stirred overnight at room temperature. Water (500 ml) was added and the mixture stirred for 30 minutes then the aqueous layer was separated and treated with solid sodium hydroxide to give pH 14. The solution was boiled for 90 minutes, cooled to room temperature and acidified to pH 1–2 with conc. HCl. The acidic solution was extracted with dichloromethane and the combined extracts dried, then concentrated to give a red oil. The oil was treated with 1M aqu. NaOH, extracted with dichloromethane and the aqueous layer separated and treated with conc. HCl acid to give an oil. The oil was extracted into dichloromethane and the combined extracts dried, then concentrated to give the desired product as an orange-red oil (83.4 g). $^1$H NMR consistent with proposed structure.

(h) 2-(2-Amino-2-ethylhexylthio)benzophenone

The product from (g) was dissolved in methanol (to a total volume of 250 ml) and an equimolar amount of the product from (f) in methanol (total volume 120 ml) was added over 20 minutes. The mixture was stirred at room temperature for 75 minutes then concentrated in vacuo to give a dark red oil. This oil was taken up in diethyl ether (400 ml) and filtered to remove contaminating solids. The desired product was left as a solution in ether for use in (i). $^1$H NMR consistent with proposed structure.

(i) 3-Ethyl-3-butyl-5-phenyl-2,3-dihydrobenzothiazepine

1M Ethereal hydrochloric acid (275 ml) was added to a solution of the product from (h) (85.0 g) in diethyl ether and the mixture was concentrated in vacuo. The residue was azeotropically distilled by addition of 2,6-lutidine (175 ml) and refluxing in a Dean-Stark apparatus overnight. The mixture was concentrated in vacuo, neutralised by addition of 5% sodium bicarbonate then the minimum volume of ethyl acetate was added to dissolve the red oil. The organic layer was separated, washed with brine, dried and concentrated. The crude residue was purified by column chromatography on silica using toluene as eluant. Concentration of the relevant fractions gave the desired product (63.7 g). $^1$H NMR consistent with the proposed structure.

(j) (+-)-Trans-3-butyl-3-ethyl-2,3,4,5-tetrahydro-5-phenyl-1,4-benzothiazepine

1M Diborane (211 ml in THF) was added over 45 minutes to a solution of the product from (i) (63.7 g) in THF under nitrogen. Reaction was stirred at room temperature for 17 hours. 50% Hydrochloric acid (125 ml) was added and the mixture was concentrated in vacuo. The residue was partitioned between aqu. NaOH and ethyl acetate. The organic layer was dried and concentrated to give an orange-yellow oil (67.5 g) comprising cis and trans isomers which was chromatographed on silica using toluene as eluant to give the desired product as a pale yellow oil (27.3 g). $^1$H NMR consistent with the proposed structure.

(k) (+-)-Trans-3-butyl-3-ethyl-2,3,4,5-tetrahydro-5-phenyl-1,4-benzothiazepine 1,1-dioxide 30% Aqueous hydrogen peroxide (73.1 g) and trifluoroacetic acid (TFA) (225 ml) were cooled and a solution of the product from (j) (70.0 g) in TFA (200 ml) was added. The reaction was stirred at room temperature for 24 hours, then added to water (1000 ml) and basified with solid sodium hydroxide. The resulting insoluble solid was filtered off, warmed with 1M aqu. NaOH and extracted into ethyl acetate. The combined extracts were evaporated in vacuo to give the desired product (69.0 g). $^1$H NMR consistent with the proposed structure.

(l) (−)-(RR)-3-Butyl-3-ethyl-2,3,4,5-tetrahydro-5-phenyl-1,4-benzothiazepine 1,1-dioxide The product from (k) (208.3 g) was mixed with diethyl ether (1500 ml) and (−)-di-p-toluoyl-L-tartaric acid (225.2 g, Schweitzerhall) in diethyl ether added. On standing, a white solid precipitated which was filtered off and recrystallised from acetone/hexane to give the desired product is the acid salt. The title compound was liberated from its salt by treatment with 1M aqu. NaOH and extracted with ethyl acetate. The combined extracts were evaporated in vacuo to give the desired product as a white solid (83.0 g), mp 115°–116° C.

Analysis: Calcd. C 70.55; H 7.61; N 3.92; S 8.97
Found: C 70.58; H 7.56; N 3.96; S 8.88

$^1$H NMR (DMSO-$d_6$), δ: 0.81–0.92 (6H, m, 2×CH$_3$); 1.15–1.40 (4H, m, 2×CH$_2$); 1.47–1.70 (3H, m, CH$_2$+ NH); 1.80–1.90 (1H, m, CH$_2$); 2.13–2.24 (1H, m, CH$_2$); 3.07–3.46 (2H, q, CH$_2$SO$_2$); 6.09 (1H, s, CH); 6.71–6.74 (1H, m, Ar-H); 7.26–7.41 (7H, m, Ar-H); 8.10–8.13 (1H, m, Ar-H)

Alternative preparation of (−)-(RR)-3-butyl-3-ethyl-2,3,4,5-tetrahydro-5-phenyl-1,4-benzothiazepine 1,1-dioxide (a) Ethyl 2-aminobutyrate hydrochloride Thionyl chloride (1.25 moles) was added to a solution of 2-aminobutyric acid (1 mole) in SD12A3 (95% ethanol/5% toluene) at a temperature of <5° C. When addition was complete, the mixture was stirred at 27° C. for 16 hours and the resulting precipitate filtered off and washed with methyl t-butyl ether to give the desired product as a white solid (97% yield).

(b) Ethyl 2-benzylideneaminobutyrate

Triethylamine (2 moles) was added to a solution of the product from step (a) (1 mole) in toluene. When addition was complete, benzaldehyde (1 mole) was added. The mixture was azeotroped until no further water was collected, then cooled to room temperature and filtered. The filtrate was evaporated in vacuo ti give the desired product as an oil.

(c) Ethyl 2-benzylideneamino-2-ethylhexanoate

A 1.6M solution of n-butyl lithium in hexane (33 mmoles, Aldrich) was added to a solution of diisopropylamine (40 mmoles) in THF (21 ml) at a temperature of 5°–10° C. When addition was complete, the mixture was added to a solution of the product from step (b) (30 mmoles) in THF (20 ml) at a temperature of 5°–10° C. When addition was complete, n-butyl iodide (40 mmoles) was added and the mixture allowed to warm to room temperature. After 20 hours, the mixture was poured into water/diethyl ether (1.1 L/0.5 L) and the organic layer separated, washed with brine (1.1 L), dried and evaporated in vacuo to give the desired product as an amber liquid (100% yield).

(d) Ethyl 2-amino-2-ethylhexanoate

A solution of the product from step (c) (1mole) in 1N aqu. HCl (1.2 moles) was stirred for 10 minutes at room temperature, then washed with toluene. The pH of the remaining aqueous phase was adjusted to 7 using 12.5% w/v sodium hydroxide, then cooled to 10° C., further basified to pH 12 and extracted with toluene. The extracts were combined, washed with brine, dried and evaporated in vacuo. The residue was distilled to give the desired product as an oil (70–80% yield).

(e) (R)-2-Amino-2-ethylhexanoic acid

A suspension of pig liver esterase (0.1 g, Sigma-Aldrich-Fluka) in water was added to an aqueous solution of the product from step (d) (100 g). When addition was complete, the pH of the mixture was adjusted to 9.7 using 1N aqu. NaOH and maintained at this value by the addition of further 1N aqu. NaOH. After the addition of a predetermined amount of 1N aqu. NaOH (85 g over 10 hours), the mixture was washed with diethyl ether to remove unreacted (S)-ethyl 2-amino-2-ethylhexanoate. The remaining aqueous phase was evaporated in vacuo to give a white solid comprising the desired product and its sodium salt (40–45% yield).

(f) (R)-2-Amino-2-ethylhexan-1-ol

The product from step (e) (20 g) was added to a 1M solution of lithium aluminium hydride (1.5 molar equivalents) in THF and the mixture refluxed for 3 hours, then stirred for 16 hours at room temperature. The mixture was cooled to about 0° C., then quenched with water and 1N aqu. NaOH added. The resulting solid was broken up with additional water and the suspension heated at 50° C. for 5 minutes, then cooled to room temperature, diethyl ether (100 ml) added and filtered. The filtrate was evaporated in vacuo to give the desired product as an oil (82% yield).

(g) (R)-2-Butyl-2-ethylaziridine

Chlorosulphonic acid (1 molar equivalent) was added to a solution of the product from step (f) (15 g) in dichloroethane (90 ml) at a temperature of <16° C. When addition was complete, the mixture was stirred for 2 hours at room temperature and then evaporated in vacuo. Water (60 ml) and 5% w/v aqu. NaOH (41 ml) were added and the mixture distilled at atmospheric pressure. The organic phase of the distillate was separated and dried over KOH to give a solution of the desired product (77% yield).

(h) 2-Thiobenzophenone

A 2.5M solution of n-butyl lithium (2 moles) in hexane was added to a solution of N,N,N',N'-tetramethylethylenediamine (TMEDA, 2 moles) in cyclohexane at a temperature of −8° to 0° C. When addition was complete, a 4.5M solution of thiophenol (1 mole) in cyclohexane was added and the temperature allowed to rise to 40°–50° C. When addition was complete, the mixture was stirred overnight at room temperature. A 4.5M solution of benzonitrile (1 mole) in cyclohexane was then added over 1 hour at a temperature of 15°–20° C. When addition was complete, the mixture was heated at 40° C. for 4 hours, then stirred at room temperature for 72 hours and quenched with water. The resulting organic phase was extracted with 1N sodium hydroxide and the combined extracts heated at 75° C. for 2.5 hours, then cooled to room temperature, acidified to pH 1 using conc. HCl and extracted four times with toluene. The combined extracts were dried and evaporated in vacuo to give a red oil which was taken up in SD3A and stirred at room temperature for 16 hours. The resulting precipitate was filtered off and washed with SD3A to give the desired product as a white solid (61% yield).

(i) (R)-3-Ethyl-3-butyl-5-phenyl-2,3-dihydrobenzothiazepine

The solution from step (g) (1.05 moles) was added to a suspension of the product from step (h) (1 mole) in 2,6-lutidine (50 ml) at a temperature of about 25° C. When addition was complete, the mixture was stirred at room temperature for 1.5 hours, then conc. HCl (6.3 ml) added. When addition was complete, the mixture was azeotroped for 3 hours, then stirred at room temperature overnight and evaporated in vacuo. The residue was taken up in 5% w/v aqu. $NaHCO_3$ and the solution extracted twice with ethyl acetate. The combined extracts were washed with brine, dried and evaporated in vacuo. The residue was chromatographed in silica gel using 95:5 hexane:ethyl acetate as eluant to give the desired product as a red-orange oil (77% yield).

(j) (RR,RS)-3-Butyl-3-ethyl-2,3,4,5-tetrahydro-5-phenyl-1,4-benzothiazepine

A 1M solution of diborane in THF (63 ml) was added to a solution of the product from step (i) (0.9 molar equivalents) in THF (100 ml) at a temperature of about 1° C. When addition was complete, the mixture was stirred overnight at room temperature, then cooled to about 0° C. and 50% v/v HCl (40 ml) added. When addition was complete, the mixture was stirred at room temperature for 1 hour, then concentrated in vacuo to remove the THF. Water (25 ml) was added to the remaining aqueous phase, the pH adjusted to 8 using 12% w/v aqu. NaOH and the solution extracted with ethyl acetate. The combined extracts were dried and evaporated in vacuo to give the desired product as a red-orange oil comprising cis and trans isomers (100% yield).

(k) (RR,RS)-3-Butyl-3-ethyl-2,3,4,5-tetrahydro-5-phenyl-1,4-benzothiazepine 1,1-dioxide A suspension of the product from step (j) (0.33 molar equivalents) in trifluoroacetic acid (25 ml) was added to a solution of 30% aqu. $H_2O_2$ (10.2 ml) in trifluoroacetic acid (20 ml) at a temperature of about 0° C. When addition was complete, the mixture was stirred overnight at room temperature, then poured into water (200 ml) to give a waxy solid which was separated and taken up in 1N aqu. NaOH. The solution was heated to 40° C. then cooled and extracted with ethyl acetate. The combined extracts were washed with 1N aqu. NaOH, dried and evaporated in vacuo to give an oil comprising the cis and trans isomers (84% yield).

(l) (−)-(RR)-3-Butyl-3-ethyl-2,3,4,5-tetrahydro-5-phenyl-1,4-benzothiazepine 1,1-dioxide A solution of (−)-di-p-toluoyl-L-tartaric acid (1 mole) in diethyl ether (20 ml) was added to a solution of the product from step (k) (1 mole) in diethyl ether (20 ml). When addition was complete, the mixture was stirred at room temperature for 2 hours and the resulting crystals filtered off, washed with diethyl ether and dried to give the (RR)-tartrate salt which was neutralised with 1N aqu. NaOH and extracted with ethyl acetate. The combined extracts were dried and evaporated in vacuo to give an oil which crystallised from hot hexanes to give the desired product as a white solid (58% yield). The mp, elemental analysis and $^1H$ NMR of the product were in agreement with those obtained by the alternative synthesis.

Preparation of (−)-(RR)-3-butyl-3-ethyl-2,3,4,5-tetrahydro-5-phenyl-1,4-benzothiazepine 1,1-dioxide hydrochloride The product from Synthetic Example 1 (0.95 g) was taken up in ether (75 ml), 10M ethereal HCl (50 ml) added and the mixture stood for 3 hours. The resulting precipitate was filtered off and dried to give the desired product as a white solid (0.86 g), mp 184°–188° C.

Analysis: Calcd. C 64.02; H 7.16; N 3.56; S 8.14
Found: C64.09; H 7.16; N 3.01; S 8.21
$^1H$ NMR (DMSO-$d_6$), δ: 0.8–0.91 (6H, m, $CH_3$); 1.00–1.04 (1H, m, $CH_2$); 1.29 (3H, b, $CH_2$); 1.92–2.00 (3H, b, $CH_2$); 2.50–2.51 (3H, b, $CH_2+NH_2$); 3.40–4.80 (4H, b, $CH_2SO_2$); 6.20 (1H, b, CH); 6.83 (1H, b, Ar-H); 7.56–7.70 (7H, b, Ar-H); 8.10 (1H, b, Ar-H)

SYNTHETIC EXAMPLES 2–64

Each of the following compounds of formula (I) was prepared by a method analogous to that of Synthetic Example 1 or by one of the other synthetic routes described herein. In all cases, $^1H$ NMR and elemental analysis were consistent with the proposed structure.

2) (+−)-Trans-3-Butyl-3-ethyl-2,3,4,5-tetrahydro-5-phenyl-1,4-benzothiazepine 1,1-dioxide, mp 98°–100° C.;

(−)-Trans-3-Methyl-3-propyl-2,3,4,5tetrahydro-5-phenyl-1,4-benzothiazepine 1,1-dioxide, mp 129°–130° C.;

4) 3-Ethyl-3-methyl-2,3,4,5-tetrahydro-5-phenyl-1,4-benzothiazepine, mp 124°–125° C.;

5) (+)-3,3-Diethyl-2,3,4,5-tetrahydro-5-phenyl-1,4-benzothiazepine 1,1-dioxide, mp 100°–102° C.;

6) 3-Butyl-2,3,4,5-tetrahydro-3-methyl-5-phenyl-1,4-benzothiazepine 1,1-dioxide, mp 103°–104° C.;

7) 3-Methyl-3-propyl-2,3,4,5-tetrahydro-5-phenyl-1,4-benzothiazepine 1,1-dioxide, mp 120°–121° C.;

8) 3,3-Diethyl-2,3,4,5-tetrahydro-5-phenyl-1,4-benzothiazepine 1,1-dioxide, mp 115°–116° C.;

9) (+)-Trans-3-Butyl-3-ethyl-2,3,4,5-tetrahydro-5-phenyl-1,4-benzothiazepine 1,1-dioxide, mp 101° C.;

10) (+)-Trans-2,3,4,5-Tetrahydro-3-methyl-5-phenyl-3-propyl-1,4-benzothiazepine 1,1-dioxide, mp 129°–130° C.;

11) (−)-3,3-Diethyl-2,3,4,5-tetrahydro-5-phenyl-1,4-benzothiazepine 1,1-dioxide, mp 101°–103° C.;

12) 3-Ethyl-2,3,4,5-tetrahydro-3-methyl-5-phenyl-1,4-benzothiazepine, mp 110°–112° C.;

13) 3-Ethyl-2,3,4,5-tetrahydro-3-methyl-5-phenyl-1,4-benzothiazepine hydrochloride 0.25 $H_2O$, mp 162°–164° C. (eff.);

14) 3-Ethyl-2,3,4,5-tetrahydro-3-methyl-5-phenyl-1,4-benzothiazepine 1,1-dioxide, mp 128°–129° C.;

15) 3,3-Diethyl-2,3,4,5-tetrahydro-5-phenyl-1,4-benzothiazepine hydrochloride, mp 211°–214° C.;

16) (+−)-2,3,4,5-Tetrahydro-3-methyl-5-phenyl-3-propyl-1,4-benzothiazepine, mp 101°–103° C.;

17) 2,3,4,5-Tetrahydro-3-methyl-5phenyl-3-propyl-1,4-benzothiazepine, mp 72°–74° C.;

18) 3-Ethyl-2,3,4,5-tetrahydro-5-phenyl-3-propyl-1,4-benzothiazepine hydrochloride 0.25 $H_2O$, mp 205°–207° C.;

19) 3-Ethyl-2,3,4,5-tetrahydro-5-phenyl-3-propyl-1,4-benzothiazepine 1,1-dioxide 0.25 $H_2O$, mp 115°–118° C.;

20) 2,3,4,5-Tetrahydro-5-phenyl-3,3-dipropyl-1,4-benzothiazepine hydrochloride, 209°–211° C.;

21) 3-Ethyl-2,3,4,5-tetrahydro-5-phenyl-3-propyl-1,4-benzothiazepine 1,1-dioxide hydrochloride 0.33 $H_2O$, 206°–209° C.;

22) 2,3,4,5-Tetrahydro-5-phenyl-3,3-dipropyl-1,4-benzothiazepine 1,1-dioxide, mp 104°–106° C.;

23) 3,3-Dibutyl-2,3,4,5-tetrahydro-5-phenyl-1,4-benzothiazepine hydrochloride, mp 209°–212° C.;
24) 3-Butyl-2,3,4,5-tetrahydro-3-methyl-5-phenyl-1,4-benzothiazepine hydrochloride, mp 203°–205° C.;
25) 3-Butyl-3-ethyl-2,3,4,5-tetrahydro-5-phenyl-1,4-benzothiazepine hydrochloride, mp 205°–207° C.;
26) 3-Butyl-3-ethyl-2,3,4,5-tetrahydro-5-phenyl-1,4-benzothiazepine 1,1-dioxide hydrochloride, mp 209°–212° C.;
27) 2,3,4,5-Tetrahydro-3-methyl-3-pentyl-5phenyl-1,4-benzothiazepine maleate, mp 182°–183° C.;
28) 3-Ethyl-2,3,4,5-tetrahydro-5-phenyl-3-propyl-1,4-benzothiazepine hydrochloride, mp 198°–200° C.;
29) (+-)-Cis-3-Butyl-3-ethyl-2,3,4,5-tetrahydro-7-methyl-5-phenyl-1,4-benzothiazepine 1,1-dioxide, mp 138°–140° C.;
30) (+-)-Cis-3-Butyl-3-ethyl-2,3,4,5-tetrahydro-7-methoxy-5-phenyl-1,4-benzothiazepine, light yellow oil;
(31) (+-)-Trans-3-Butyl-3-ethyl-2,3,4,5-tetrahydro-7-methoxy-5-phenyl-1,4-benzothiazepine, light yellow oil;
32) (+-)-Cis-3-Butyl-3-ethyl-2,3,4,5-tetrahydro-7-methoxy-5-phenyl-1,4benzothiazepine 1,1-dioxide, mp 113°–115° C.;
33) (--)-Cis-3-Butyl-3-ethyl-2,3,4,5-tetrahydro-7-methoxy-5-phenyl-1,4-benzothiazepine 1-oxide, mp 103°–105° C.;
34) (+-)-Trans-3-Butyl-3-ethyl-2,3,4,5-tetrahydro-7-methoxy-5-phenyl-1,4-benzothiazepine 1-dioxide hydrochloride, mp 199°–201° C.;
35) (+-)-Trans-3-Butyl-3-ethyl-5-phenyl-2,3,4,5-tetrahydro-1,4-benzothiazepine 1-oxide, mp 98°–101° C.;
36) (+-)-Trans-3-Butyl-3-ethyl-2,3,4,5-tetrahydro-5-phenyl-1,4benzothiazepine 1-oxide, mp 133°–136° C.;
37) (+-)-Cis-7-Chloro-3-butyl-3-ethyl-2,3,4,5-tetrahydro-5-phenyl-1,4-benzothiazepine 0.4 toluene, light yellow oil;
38) (+-)-Trans-7-Chloro-3-butyl-3-ethyl-2,3,4,5-tetrahydro-5-phenyl-1,4-benzothiazepine 0.3 toluene, light yellow oil;
39) (--)-Trans-3-Butyl-7-Chloro-3-ethyl-2,3,4,5-tetrahydro-5-phenyl-1,4-benzothiazepine 1,1-dioxide, mp 100°–102° C.;
40) (+-)-Trans-3-Butyl-3-ethyl-2,3,4,5-tetrahydro-5-(4-methoxyphenyl)-1,4-benzothiazepine 1,1-dioxide hydrochloride, mp 194°–196° C.;
41) (+-)-Trans-3-Butyl-3-ethyl-2,3,4,5-tetrahydro-5-(4-tolyl)-1,4-benzothiazepine 1,1-dioxide hydrochloride, mp 204°–206° C.;
42) (+-)-Cis-3-Butyl-3-ethyl-2,3,4,5-tetrahydro-5-(4-tolyl)-1,4-benzothiazepine 1,1-dioxide, mp 155°–156° C.;
43) (+-)-Cis-3-Butyl-3-ethyl-2,3,4,5-tetrahydro-5-(4-methoxyphenyl)-1,4-benzothiazepine, mp 75°–77° C.;
44) (+-)-Cis-3-Butyl-3-ethyl-2,3,4,5-tetrahydro-5-(4-methoxyphenyl)-1,4-benzothiazepine 1,1-dioxide, mp 109°–111° C.;
45) (+-)-Cis-3-Butyl-3-ethyl-5-(4-fluorophenyl)-2,3,4,5-tetrahydro-1,4-benzothiazepine, mp 76°–78° C.;
46) (+-)-Trans-3-Butyl-5-(3,4-dichlorophenyl)-3-ethyl-2,3,4,5-tetrahydro-1,4-benzothiazepine, mp 98°–100° C.;
47) (+-)-Trans-3-Butyl-5-(4-chlorophenyl)-3-ethyl-2,3,4,5-tetrahydro-1,4-benzothiazepine 1,1-dioxide hydrochloride 0.3 $H_2O$, mp 178°–180° C.;
48) (+-)-Cis-3-Butyl-5-(4-chlorophenyl)-5-ethyl-2,3,4,5-tetrahydro-1,4-benzothiazepine 1,1-dioxide hydrochloride, mp 186°–188° C.;
49) Trans-3-Butyl-3-ethyl-2,3,4,5-tetrahydro-5-(3-nitrophenyl)-1,4-benzothiazepine 1,1-dioxide, mp 139°–142° C.;
50) Trans-3-Butyl-3-ethyl-2,3,4,5-tetrahydro-5-(4-nitrophenyl)-1,4-benzothiazepine 1,1-dioxide, mp 139°–142° C.;
51) (+-)-Trans-5-(4-Benzyloxyphenyl)-3-butyl-3-ethyl-2,3,4,5-tetrahydro-1,4-benzothiazepine 1,1-dioxide, mp 94°–95° C.;
52) (+-)-Cis-5-(4-Benzyloxyphenyl)-3-butyl-3-ethyl-2,3,4,5-tetrahydro-1,4-benzothiazepine 1,1-dioxide, mp 137°–138° C.;
53) (+-)-Trans-5-(4-Benzyloxyphenyl)-3-butyl-3-ethyl-2,3,4,5-tetrahydro-1,4-benzothiazepine, mp 97°–98° C.;
54) (+-)-Trans-3-(4-(3-Butyl-3-ethyl-2,3,4,5-tetrahydro-1,4-benzothiazepine-5-yl)phenoxy)propanesulphonic acid 1,1-dioxide, mp 270° C. (dec.);
55) (+-)-Trans-3-Butyl-3-ethyl-2,3,4,5-tetrahydro-5-(2-fluorophenyl)-1,4-benzothiazepine 1,1-dioxide, hydrochloride, mp 194°–196° C.;
56) (+-)-Trans-3-Butyl-3-ethyl-2,3,4,5-tetrahydro-5-(3-fluorophenyl)-1,4-benzothiazepine 1,1-dioxide, mp 143°–145° C.;
57) (+-)-Cis-3-Butyl-3-ethyl-2,3,4,5-tetrahydro-5-(4-pyridyl)-1,4-benzothiazepine 1,1-dioxide, mp 121°–123° C.;
58) (+-)-Trans-3-Butyl-3-ethyl-2,3,4,5-tetrahydro-5-(4-pyridyl)-1,4-benzothiazepine 1,1-dioxide, mp 110°–111° C.;
59) (+-)-Cis-3-Butyl-3-ethyl-2,3,4,5tetrahydro-5-(4-trifuloromethylphenyl)-1,4-benzothiazepine 1,1-dioxide, mp 64°–65° C.;
60) (+-)-Trans-3-Butyl-3-ethyl-2,3,4,5-tetrahydro-5-(3-trifluoromethylphenyl)-1,4-benzothiazepine 1,1-dioxide, mp 110°–112° C.;
61) (--)-Trans-3-Butyl-3-ethyl-2,3,4,5-tetrahydro-5-(3,4-difluorophenyl)-1,4-benzothiazepine 1,1-dioxide, mp 205°–215° C.;
62) (+-)-Trans-3-Butyl-3-ethyl-2,3,4,5-terahydro-5-(2,4-difluorophenyl)-1,4-benzothiazepine 1,1-dioxide, ml 97°–99° C.;
63) (+-)-Trans-3-isopentyl-3-ethyl-2,3,4,5-tetrahydro-5-phenyl-1,4-benzothiazepine 1,1-dioxide, mp 86°–87° C.; and
64) (+-)-Cis-3-isopentyl-3-ethyl-2,3,4,5-tetrahydro-5-phenyl-1,4-benzothiazepine 1,1-dioxide, mp 123°–125° C.

PHARMACEUTICAL COMPOSITION EXAMPLES

In the following Examples, the active compound can be any compound of formula (I) and/or a pharmaceutically acceptable salt, solvate, or physiologically functional derivative thereof. The active compound is preferably (−)-(RR)-3-butyl-3-ethyl-2,3,4,5-tetrahydro-5-phenyl-1,4-benzothiazepine or one of the compounds of Synthetic Examples 2 to 64.

(i) Tablet compositions

The following compositions A and B can be prepared by wet granulation of ingredients (a) to (c) and (a) to (d) with a solution of povidone, followed by addition of the magnesium stearate and compression.

Composition A

|  | mg/tablet | mg/tablet |
|---|---|---|
| (a) Active ingredient | 250 | 250 |
| (b) Lactose B.P. | 210 | 26 |
| (c) Sodium Starch Glycollate | 20 | 12 |
| (d) Povidone B.P. | 15 | 9 |
| (e) Magnesium Stearate | 5 | 3 |
|  | 500 | 300 |

Composition B

|  | mg/tablet | mg/tablet |
|---|---|---|
| (a) Active ingredient | 250 | 250 |
| (b) Lactose 150 | 150 | — |
| (c) Avicel PH 101 | 60 | 26 |
| (d) Sodium Starch Glycollate | 20 | 12 |
| (e) Povidone B.P. | 15 | 9 |
| (f) Magnesium Stearate | 5 | 3 |
|  | 500 | 300 |

Composition C

|  | mg/tablet |
|---|---|
| Active ingredient | 100 |
| Lactose | 200 |
| Starch | 50 |
| Povidone | 5 |
| Magnesium Stearate | 4 |
|  | 359 |

The following compositions D and E can be prepared by direct compression of the admixed ingredients. The lactose used in composition E is of the direct compression type.

Composition D

|  | mg/tablet |
|---|---|
| Active ingredient | 250 |
| Magnesium Stearate | 4 |
| Pregelatinised Starch NF15 | 146 |
|  | 400 |

Composition E

|  | mg/tablet |
|---|---|
| Active ingredient | 250 |
| Magnesium Stearate | 5 |
| Lactose | 145 |
| Avicel | 100 |
|  | 500 |

Composition F (Controlled release composition)

|  | mg/tablet |
|---|---|
| (a) Active ingredient | 500 |
| (b) Hydroxypropylmethylcellulose (Methocel K4M Premium) | 112 |
| (c) Lactose B.P. | 53 |
| (d) Povidone B.P.C. | 28 |
| (e) Magnesium Stearate | 7 |
|  | 700 |

The composition can be prepared by wet granulation of ingredients (a) to (c) with a solution of povidone, followed by addition of the magnesium stearate and compression.

Composition G (Enteric-coated tablet)

Enteric-coated tablets of Composition C can be prepared by coating the tablets with 25 mg/tablet of an enteric polymer such as cellulose acetate phthalate, polyvinylacetate phthalate, hydroxypropylmethyl-cellulose phthalate, or anionic polymers of methacrylic acid and methacrylic acid methyl ester (Eudragit L). Except for Eudragit L, these polymers should also include 10% (by weight of the quantity of polymer used) of a plasticizer to prevent membrane cracking during application or on storage. Suitable plasticizers include diethyl phthalate, tributyl citrate and triacetin.

Composition H (Enteric-coated controlled release tablet)

Enteric-coated tablets of Composition F can be prepared by coating the tablets with 50 mg/tablet of an enteric polymer such as cellulose acetate phthalate, polyvinylacetate phthalate, hydroxypropylmethyl-cellulose phthalate, or anionic polymers of methacrylic acid and methacrylic acid methyl ester (Eudragit L). Except for Eudragit L, these polymers should also include 10% (by weight of the quantity of polymer used) of a plasticizer to prevent membrane cracking during application or on storage. Suitable plasticizers include diethyl phthalate, tributyl citrate and triacetin.

(ii) Capsule compositions

Composition A

Capsules can be prepared by admixing the ingredients of Composition D above and filling two-part hard gelatin capsules with the resulting mixture. Composition B (infra) may be prepared in a similar manner.

Composition B

|  | mg/capsule |
|---|---|
| (a) Active ingredient | 250 |
| (b) Lactose B.P. | 143 |
| (c) Sodium Starch Glycollate | 25 |
| (d) Magnesium Stearate | 2 |
|  | 420 |

Composition C

|  | mg/capsule |
|---|---|
| (a) Active ingredient | 250 |
| (b) Macrogol 4000 BP | 350 |
|  | 600 |

Capsules can be prepared by melting the Macrogol 4000 BP, dispersing the active ingredient in the melt and filling two-part hard gelatin capsules therewith.

|  | mg/capsule |
| --- | --- |
| Active ingredient | 250 |
| Lecithin | 100 |
| Arachis Oil | 100 |
|  | 450 |

Capsules can be prepared by dispersing the active ingredient in the lecithin and arachis oil and filling soft, elastic gelatin capsules with the dispersion.

|  | mg/capsule |
| --- | --- |
| (a) Active ingredient | 250 |
| (b) Microcrystalline Cellulose | 125 |
| (c) Lactose BP | 125 |
| (d) Ethyl Cellulose | 13 |
|  | 513 |

The controlled release capsule composition can be prepared by extruding mixed ingredients (a) to (c) using an extruder, then spheronising and drying the extrudate. The dried pellets are coated with a release controlling membrane (d) and filled into two-part, hard gelatin capsules.

|  | mg/capsule |
| --- | --- |
| (a) Active ingredient | 250 |
| (b) Microcrystalline Cellulose | 125 |
| (c) Lactose BP | 125 |
| (d) Cellulose Acetate Phthalate | 50 |
| (e) Diethyl Phthalate | 5 |
|  | 555 |

The enteric capsule composition can be prepared by extruding mixed ingredients (a) to (c) using an extruder, then spheronising and drying the extrudate. The dried pellets are coated with an enteric membrane (d) containing a plasticizer (e) and filled into two-part, hard gelatin capsules.

Composition G (Enteric-coated controlled release capsule)

Enteric capsules of Composition E can be prepared by coating the controlled-release pellets with 50 mg/capsule of an enteric polymer such as cellulose acetate phthalate, polyvinylacetate phthalate, hydroxypropylmethylcellulose phthalate, or anionic polymers of methacrylic acid and methacrylic acid methyl ester (Eudragit L). Except for Eudragit L, these polymers should also include 10% (by weight of the quantity of polymer used) of a plasticizer to prevent membrane cracking during application or on storage. Suitable plasticizers include diethyl phthalate, tributyl citrate and triacetin.

(iii) Intravenous injection composition

| Active ingredient | 0.200 g |
| --- | --- |
| Sterile, pyrogen-free phosphate buffer | (pH 9.0) to 10 ml |

The active ingredient is dissolved in most of the phosphate buffer at 35°–40° C., then made up to volume and filtered through a sterile micropore filter into sterile 10 ml glass vials (Type 1) which are sealed with sterile closures and overseals.

(iv) Intramuscular injection composition

| Active ingredient | 0.20 g |
| --- | --- |
| Benzyl Alcohol | 0.10 g |
| Glycofurol 75 | 1.45 g |
| Water for Injection | q.s. to 3.00 ml |

The active ingredient is dissolved in the glycofurol. The benzyl alcohol is then added and dissolved, and water added to 3 ml. The mixture is then filtered through a sterile micropore filter and sealed in sterile 3 ml glass vials (Type 1).

(v) Syrup composition

| Active ingredient | 0.25 g |
| --- | --- |
| Sorbitol Solution | 1.50 g |
| Glycerol | 1.00 g |
| Sodium Benzoate | 0.005 g |
| Flavour | 0.0125 ml |
| Purified Water | q.s. to 5.0 ml |

The sodium benzoate is dissolved in a portion of the purified water and the sorbitol solution added. The active ingredient is added and dissolved. The resulting solution is mixed with the glycerol and then made up to the required volume with the purified water.

(vi) Suppository composition

|  | mg/suppository |
| --- | --- |
| Active ingredient | 250 |
| Hard Fat, BP (Witepsol H15 - Dynamit NoBel) | 1770 |
|  | 2020 |

One-fifth of the Witepsol H15 is melted in a steam-jacketed pan at 45° C. maximum. The active ingredient is sifted through a 200 μm sieve and added to the molten base with mixing, using a Silverson fitted with a cutting head, until a smooth dispersion is achieved. Maintaining the mixture at 45° C. the remaining Witepsol H15 is added to the suspension which is stirred to ensure a homogenous mix. The entire suspension is then passed through a 250 μm stainless steel screen and, with continuous stirring, allowed to cool to 40° C. At a temperature of 38°–40° C. 2.02 g aliquots of the mixture are filled into suitable plastic moulds and the suppositories allowed to cool to room temperature.

(vii) Pessary composition

|  | mg/pessary |
| --- | --- |
| Active ingredient (63 μm) | 250 |
| Anhydrous Dextrose | 380 |
| Potato Starch | 363 |
| Magnesium Stearate | 7 |
|  | 1000 |

The above ingredients are mixed directly and pessaries prepared by compression of the resulting mixture.

(viii) Transdermal composition

| Active ingredient | 200 mg |
| --- | --- |
| Alcohol USP | 0.1 ml |
| Hydroxyethyl cellulose |  |

The active ingredient and alcohol USP are gelled with hydroxyethyl cellulose and packed in a transdermal device with a surface area of 10 cm$^2$.

Biological Assay
In vitro inhibition of bile acid uptake

Freshly prepared rat distal ileal brush border membrane vesicles (about 200 mg vesicle protein) were incubated for 30 seconds at 24° C. in an incubation mixture comprising 10 $\mu$M $^3$H taurocholate, 100 mM NaCl (or KCl) and 80 mM mannitol in 20 mM Hepes Tris pH 7.4. Each test compound was dissolved in ethanol (or water) and then diluted with incubation mixture to an ethanol concentration of not more than 1% v/v. The incubation was terminated by rapid dilution and filtration and the filter washed with an ice-cold isotonic sodium-free buffer.

The uptake of $^3$H taurocholate was measured by the radioactivity remaining on the filter and converted to pmoles/mg vesicle protein. The active, i.e. sodium-dependent, uptake was obtained by subtracting the passive uptake measured in 100 mM KCl from the total uptake measured in 100 mM NaCl. The active uptake for each test compound was compared with a control active uptake and the results expressed at % inhibition of bile acid uptake.

For the compound of Synthetic Example 1, the % inhibition of bile acid uptake at concentrations of 10, 3, 1 and 0.3 $\mu$M was 96, 85, 69 and 55% respectively.

I claim:

1. A method for the preparation of a compound of formula (I)

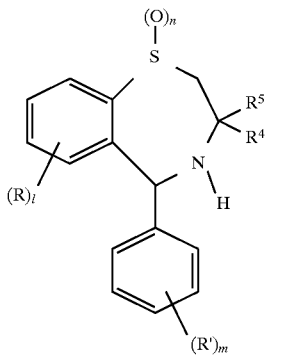

wherein
  l is an integer of from 0 to 4;
  m is an integer of from 0 to 5;
  n is an integer of from 0 to 2;
  R and R' are atoms or groups independently selected from halogen, nitro, phenylalkoxy, $C_{1-4}$ alkoxy, $C_{1-6}$ alkyl and —$O(CH_2)_pSO_3R"$ wherein p is an integer of from 1 to 4 and R" is hydrogen or $C_{1-6}$ alkyl, wherein said phenylalkoxy, alkoxy and alkyl groups are optionally substituted by one or more halogen atoms;
  $R^4$ is a $C_{1-6}$ straight alkyl group; and
  $R^5$ is a $C_{2-6}$ straight alkyl group;

which comprises:
reducing the imine bond of a compound of formula (II)

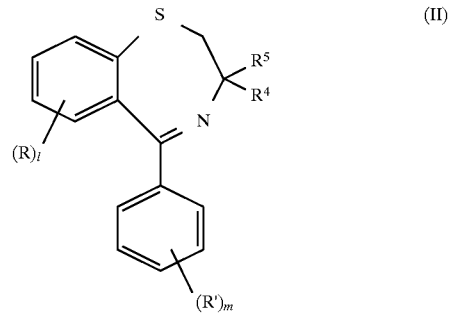

wherein l, m, R, R', $R^4$, $R^5$ are as hereinbefore defined;

and optionally oxidising the compound of formula (I) so obtained to the corresponding compound wherein n=1 or 2 followed by optional conversion to a salt, solvate, or physiologically functional derivative thereof.

2. A compound of formula (II)

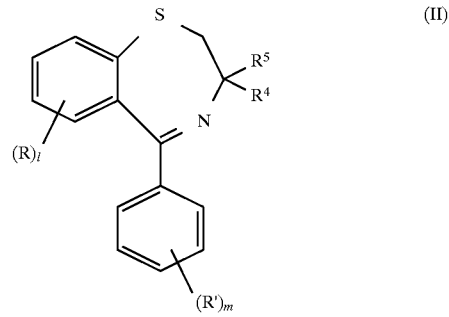

wherein
  l is an integer of from 0 to 4;
  m is an integer of from 0 to 5;
  R and R' are atoms or groups independently selected from halogen, nitro, phenylalkoxy, $C_{1-4}$ alkoxy, $C_{1-6}$ alkyl and —$O(CH_2)_pSO_3R"$ wherein p is an integer of from 1 to 4 and R" is hydrogen or $C_{1-6}$ alkyl, wherein said phenylalkoxy, alkoxy and alkyl groups are optionally substituted by one or more halogen atoms;
  $R^4$ is a $C_{1-6}$ straight alkyl group;
  $R^5$ is a $C_{2-6}$ straight alkyl group;
and salts, solvates and physiologically functional derivatives thereof.

* * * * *